United States Patent [19]

Baudry et al.

[11] Patent Number: 5,189,151
[45] Date of Patent: Feb. 23, 1993

[54] HIGHLY SPECIFIC DNA PROBE FOR ENTEROAGGREGATIVE ESCHERICHIA COLI

[76] Inventors: Bernadette Baudry, 631 Concerto La., Silver Spring, Md. 20902; Myron M. Levine, 5209 Windmill La., Columbia, Md. 21044

[21] Appl. No.: 524,100

[22] Filed: May 16, 1990

[51] Int. Cl.$^5$ ............................................. C07H 21/04
[52] U.S. Cl. ...................................... 536/24.32; 435/6
[58] Field of Search ................................... 536/27-29; 435/6

[56] References Cited

PUBLICATIONS

Bilge et al., J. Bacteriol. 171(8):4281 (1989).
Austerberry et al., *Mol. Cell. Biol.*, 7(1), 435-443 (1987).
Clark-Walker et al., *Embo J.*, 4(2), 465-473 (1985).
de Zamaroczy et al., *Gene*, 47, 155-177 (1986).
Nataro et al., "Detection of an Adherence Factor of Enteropathogeniv *Escherichia coli* with a DNA Probe", The Journal of Infectious Diseases, vol. 152, No. 3, Sep. 1985, pp. 560-565.
Baldini et al., "Plasmid-Mediated Adhesion in Enteropathogenic *Escherichia coli*", Journal of Pediatric-Gastroenterology and Nutrition, 2:534-538, 1983.
Nataro et al., "Patterns of adherence of diarrheagenic *Escherichia coli* to HEp-2 cells", Pediatr. Infect. Dia. J. 6:829-831, 1987.
Levine et al., "Use of DNA Probes and HEp-2 Cell Adherence Assay to Detect Diarrheagenic *Escherichia coli*", Journal of Infectious Diseases, vol. 158, No. 1, Jul. 1988, pp. 224-228.
Gomes et al., "Prevalence of *Escherichia coli* Strains with Localized, Diffuse, and Aggregative Adherence to HeLa Cells in Infants with Diarrhea and Matched Controls", Journal of Clinical Microbiology, Feb., 1989, pp. 266-269.
Mathewson, et al., "Enteroadherent *Escherichia coli* as a Cause of Diarrhea among Children in Mexico", Journal of Clinical Microbiology, Oct. 1987, pp. 1917-1919.
Mathewson et al., "A Newly Recognized Cause of Travelers' Diarrhea: Enteroadherent *Escherichia coli*", The Journal of Infectious Diseases, vol. 151, No. 3, Mar. 1985, pp. 471-475.
Cravioto et al., "Prospective study of diarrhoeal disease in a cohort of rural Mexican children: incidence and isolated pathogens during the first two years of life", Epiderm. Inf. (1988) 101, 123-134.
Vial et al., "Characterization of Enteroadherent-Aggregative *Escherichia coli*, a Putative Agent of Diarrheal Disease", Journal of Infectious Diseases, vol. 158, No. 1, Jul. 1988, pp. 70-79.
Moseley et al., "Identification of Enterotoxignic *Escherichia coli* by Colony Hybridization Using Three Enterotoxin Gene Probes", Journal of Infectious Diseases, vol. 145, No. 6, Jun. 1982, 863-869.
Wood et al., "Comparison of DNA Probes and the Sereny Test for Identification of Invasive *Shigella* and *Escherichia coli* strains", Journal of Clinical Microbiology, Sep. 1986, pp. 498-500.

*Primary Examiner*—Johnnie R. Brown
*Assistant Examiner*—L. Eric Crane

[57] ABSTRACT

An oligonucleotide comprises a DNA segment capable of hybridizing to DNA from enteroaggregative *E. coli* bacteria with high sensitivity and specificity. A recombinant vector comprises a vector carrying the oligonucleotide of the invention, the vector being capable of replication in a host. A host is transformed with the recombinant vector of the invention. A method of detecting the presence of enteroaggregative *E. coli* DNA in a biological sample with high sensitivity and specificity comprises adding to the sample the labeled oligonucleotide of the invention under conditions effective to promote hybridization thereof to the sample's DNA, and detecting the presence of hybridized labeled DNA. A method of detecting the presence of enteroaggregative *E. coli* RNA in a sample with high sensitivity and specificity comprises adding to the sample the oligonucleotide of the invention under conditions effective to promote hybridization thereof to the sample's RNA and detecting the presence of hybridized labeled RNA-DNA. An article of manufacture comprises in separate containers the oligonucleotide of the invention, a denaturing solution, a rinsing solution, filter paper, and the like and optionally a further oligonucleotide comprising a further DNA segment selected from the group consisting of enteropathogenic, enterotoxicogenic, enteroinvasive and enterohemorrhagic *E. coli* DNA and *E. coli* DNA exhibiting diffuse adherence. An article of manufacture comprises in separate containers the recombinant vector of the invention, a denaturing solution, a rinsing solution, filter paper, and the like and optionally a further oligonucleotide comprising a further DNA segment selected from the group consisting of enteropathogenic, enterotoxicogenic, enteroinvasive and enterohemorrhagic *E. coli* DNA and *E. coli* DNA exhibiting diffuse adherence.

11 Claims, No Drawings

HIGHLY SPECIFIC DNA PROBE FOR ENTEROAGGREGATIVE ESCHERICHIA COLI

TECHNICAL FIELD

This invention relates to *Escherichia coli (E. coli)* bacteria, an d more particularly to enteroaggregative *E. coli* bacteria (EAggEC), the presence of which has been associated with diarrhea. More particularly, this invention relates to the isolation and/or synthesis of an oligonucleotide which is capable of recognizing enteroaggregative *E. coli* with high sensitivity and specificity. The oligonucleotide may be utilized by itself or cloned into a recombinant vector as a probe for screening samples obtained from a large population in a simple and inexpensive manner. These characteristics make the present technology particularly suitable for application in developing countries. The present probe has a sensitivity of about 90% or greater for the detection of enteroaggregative *E. coli* and can discriminate this bacterium from enteropathogenic, enterotoxigenic, enteroinvasive and enterohemorrhagic *E. coli* with a specificity greater than 98%.

DESCRIPTION OF THE BACKGROUND

The ability of some of the strains of *Escherichia coli* to attach to HEp-2 cells in tissue culture has been correlated with their capacity to cause diarrheal illness. Three distinct patterns of adherence to HEp-2 cells have been described by investigators at the Center for Vaccine Development of the University of Maryland School of Medicine:

(1) localized adherence,
(2) diffuse adherence, and
(3) aggregative adherence.

The ability of *E. coli* strains to manifest localized adherence is dependent on the presence of a plasmid, the EPEC Adherence Factor (EAF) plasmid. The property of localized adherence is characteristic of a category of diarrheagenic *E. coli* referred to a enteropathogenic *E. coli* (EPEC). In several recent studies it has been shown that *E. coli* strains that manifest localized adherence are found significantly more often in cases of infant diarrhea than in matched controls The genes responsible for the diffuse pattern of adherence to HEp-2 cells appear to be located in the chromosome. While *E. coli* that manifest the diffuse adherence pattern clearly represent a distinct category of *E. coli*, there is much disagreement as to whether they are associated with diarrhea. In some studies strains exhibiting diffuse adherence have been found significantly more often in test cases than in controls However, in several other studies this has not been found to be so the case.

*E. coli* that show the aggregative pattern in the HEp-2 cell assay (enteroaggregative *E. coli*) have been incriminated in two separate studies as diarrheal pathogens.

In 1987, one of the present inventors at the University of Maryland coined the term enteroadherent aggregative *E. coli* to refer to the bacterium exhibiting aggregative behavior in the HEp-2 cell assay. The group characterized the *E. coli* strains and considered them a putative new category of diarrhoegenic *E. coli* (Vial, P. A., et al., supra). In subsequent publications the term was shortened from enteroadherent aggregative *E. coli* to enteroaggregative *E. coli*. These enteroaggregative *E. coli* are distinct from the other categories of diarrheagenic *E. coli* in that they have the ability to attach to HEp-2 cells in tissue culture with a particular, "aggregative", pattern. This ability has been correlated to their capacity to cause diarrheal illness.

There are several features of enteroaggregative *E. coli* bacteria that show them to be distinct from other categories of diarrheagenic *E. coli* (Vial, P. A., Robins-Browne, R., Lior, H., Prado, V., Kaper, J. B., Elsayed, A., Levine, M. M., "Characterization of enteroadherent-aggregative *Escherichia coli*, a putative agent of diarrheal disease", J. Infect. Dis. 158:70–79 (1988), the entire content of which is incorporated herein by reference). Enteroaggregative *E. coli* possess a virulence plasmid that is distinct from the virulence plasmids of other diarrheagenic *E. coli* and fall into O:H serotypes that are distinct from other categories of diarrheagenic *E. coli*. Moreover, in animal models, enteroaggregative *E. coli* cause histopathological changes that are distinct from those caused by other categories of diarrheagenic *E. coli*.

In a study conducted in Santiago, Chile, enteroaggregative *E. coli* were isolated significantly more often from symptomatic cases than from matched controls. In another study carried out in rural India enteroaggregative *E. coli* were found significantly more often in cases of persistent diarrhea (>14 days duration) (30%) than in cases of acute diarrhea (12.8%) or controls (9.9%). However, in a study undertaken in Brazil, enteroaggregative *E. coli* were isolated with similar frequency from cases of acute diarrhea and controls.

In recent years, DNA probes have been developed for identifying many of the categories of diarrheagenic *E. coli* common in epidemiologic studies. Sensitive, specific and reliable DNA probes already exist for dentifying enteropathogenic, enterotoxigenic, enteroinvasive and enterohemorrhagic *E. coli* as well as for *E. coli* exhibiting diffused and localized adherence to HEp-2 cells (Nataro, J. P., Baldini, M. M., Kaper, J. B., Black, R. E., Bravo, N., Levine, M. M., "Detection of an adherence factor of enteropathogenic *Escherichia coli* with a DNA probe", J. Infect. Dis., 152:560–565 (1985); Levine, M. M. et al, "Use of DNA probes and HEp-2 cell adherence assay to detect diarrheagenic *E. coli*", J. Infect. Dis., 158:224–228 (1988); Echeverria, P. et al, "Case-control study of endemic diarrheal disease in Thai children", J. Infect. Dis. 159:543–548 (1989); Lanata, C. F. et al, "Sensitivity and specificity of DNA probes with the stool blot technique for detection of *Escherichia coli* enterotoxin", J. Infect. Dis. 152:1087–1090 (1985); Mosley, S. et al, "Identification of enterotoxigenic *Escherichia coli* by colony hybridization using three enterotoxin gene probes", J. Infect. Dis. 145:863–869 (1982); Wood, P. K. et al, "Comparison of DNA probes with the Sereny test for identification of invasive *Shigella* and *Escherichia coli* strains", J. Clin. Microbiol. 24:498–500 (1986); Levine, M. M. et al, "A DNA probe to identify enterohemorrhagic *Escherichia coli* of 0157:H7 and other serotype that cause hemorrhagic colitis and hemolytic uremic syndrome", J. Infect. Dis. 156:175–182 (1987), the entire contents of which are incorporated herein by reference).

Enteroaggregative *E. coli* (EAggEC) bacteria, however, do not hybridize with DNA probes that identify other categories of diarrheagenic *E. coli*. Presently, EAggEC bacteria can only be identified by means of a tissue culture assay and this cell assay (HEp-2) has many disadvantages among which are the following.

(1) It requires tissue culture facilities.
(2) It takes four hours to run.
(3) It is expensive.
It is not amenable to testing large numbers of the population and
(5) It is subject to observer error and therefore requires experienced personnel.

These drawbacks render the HEp-2 tissue culture assay ill suited for use in third world countries.

A previous search for a probe for enteroaggregative E. coli (EAggEC) produced a DNA fragment obtained from a plasmid from the 042 enteroaggregative E. coli strain (Vial, P.A. et al, "Characterization of EAggEC, a putative agent of diarrheal disease", J. Inf. Diseases 158(1): 70 (1988), the entire content of which is incorporated herein by reference). That fragment, however, was capable of hybridizing to no more than 20 out of 41 strains of EAggEC different from the 042 strain. This overall low sensitivity (49%) for enteroaggregative E. coli bacteria renders the 042 EAggEC fragment a poor tool for the systematic identification of enteroaggregative E. coli bacteria.

Accordingly, since the HEp-2 cell assay differentiating enteroaggregative E. coli on the basis of adherence is cumbersome, time-consuming, labor-intensive and subject to considerable error there remains a need for an easier, more reliable method which is adaptable for use in developing countries.

DISCLOSURE OF THE INVENTION

This invention relates to an oligonucleotide comprising a DNA segment capable of hybridizing to DNA from enteroaggregative E. coli bacteria with high sensitivity and specificity.

More particularly, this invention discloses a specific DNA sequence

| 1 | CCCGGGGATC | GAGTGAGACA | CATATTATAC | TCATTTCTTG | CAATAAATGC | TTATCTGTTT |
| 61 | TCGACACAGA | CTCTGGCGAA | AGACTGTATC | ATTGATAATT | TCTTTCAGAA | AAGCATCCAG |
| 121 | TTTAATTCTT | ATTCTCTTGA | TATCGAAGAG | TTAGATATTA | ATAAACATAA | CAATATAAAA |
| 181 | ACGATGTTAC | CAGATATAAA | TATAGGGTTA | GGGCAGTATA | TAAACAACAA | TCAATGGTTC |
| 241 | TCATCTATTA | CAGACAGCCA | TTTTTATTTA | TCATTATCCT | ATAATCTTCT | ATCGGCTTAT |
| 301 | GAAGCAAAAA | TGCAGAATAA | TAAATTGGAT | ATTGCTAATT | ATTTAAAATA | TATTGAAATG |
| 361 | CTTAGTGAGA | GGAACAACTA | CATAATTAAT | TTGTTCTCGG | AAATTATTAA | CTATAAGATA |
| 421 | AAAAAATCTC | ACCTGATGTT | GATGCTCGAG | AGATATAGGA | AGCTCAATAA | AGAATACGAA |
| 481 | ATTGCAAAGC | ATAAAATGTC | AATTGGATTA | ATATCTGCTC | TTGATGTAGA | GATGATATAT |
| 541 | AATATTTTAC | AAAAAATCAG | GTTTGATATT | GATGTCCTTG | AGGAGGAGGA | AAGTTTACTG |
| 601 | TCAGATAAAA | TCTCGAGAGA | ATATCATGTT | CCTGAGAGTG | CAATCCCAGA | CATTACATAT |
| 661 | CATAAGTTAA | AAGAGTGTAA | AACAGCGGAT | TTCTATACAT | TATTAGCTGA | AAACAAAAAA |
| 721 | CTCAAGATTA | AGGCTGCTGA | TATAGATAAT | GATATAAGGA | AACTATCTGA | GATCCT | functional equivalents thereof, and functional fragments thereof about 10 to 500 base pairs long.

This invention also relates to a recombinant vector which comprises a vector carrying the oligonucleotide of the invention, the vector being capable of replication in a host.

Also part of this invention is a host carrying the recombinant vector described above.

Still part of this invention is a method of detecting the presence of enteroaggregative E. coli DNA in a biological sample with high sensitivity and specificity, which comprises labeling the oligonucleotide of the invention;

adding to said sample the labeled oligonucleotide to promote hybridization thereof to the sample's DNA; and detecting the presence of hybridized labeled DNA.
In one embodiment the method is a bacterial colony blot assay.

Also part of this invention is a method of detecting the presence of enteroaggregative E. coli RNA in a biological sample with high sensitivity and specificity, which comprises labeling the oligonucleotide of the invention;

adding to the sample labeled oligonucleotide to promote hybridization thereof to the sample's RNA; and detecting the presence of hybridized labeled RNA-DNA.

Also encompassed by this invention is an article of manufacture, comprising in separate containers the oligonucleotide of this invention; and an auxiliary component selected from the group consisting of a denaturing solution, a rinsing solution, a radiolabel and filter paper; and optionally a further oligonucleotide comprising a further DNA segment selected from the group consisting of enteropathogenic, enterotoxigenic, enteroinvasive and enterohemorrhagic E. coli DNA and E. coli exhibiting diffuse adherence.

For purposes of better understanding this invention, a general glossary of terms is provided hereinbelow.

GLOSSARY

A series of specialized terms commonly utilized in molecular biology are defined herein as they are implied within the context of this invention.

HEp-2 CELLS: These are tissue culture cells utilized in an adherence assay for identification of different types of E. coli bacteria types.

EAF PLASMID: This is a plasmid which is present in E. coli strains of bacteria exhibiting localized adherence. ENTEROPATHOGENIC E. COLI (EPEC): This is a category of diarrheagenic E. coli bacteria exhibiting a localized adherence pattern when tested with HEp-2 cells.

ENTEROAGGREGATIVE E. COLI: These strains of E. coli show a correlation with diarrhea.

DIFFUSE ADHERENCE PATTERN: This is exhibited by some E. coli strains. It is not agreed as to whether these bacteria are associated with diarrhea.

LOCALIZED ADHERENCE PATTERN: This is exhibited by enteropathogenic E. coli (EPEC) in the HEp-2 assay.

AGGREGATIVE PATTERN: This pattern is exhibited by a enteroaggregative E. coli in the presence of HEp-2 cells in culture.

HOMOLOGOUS DNA: Is a DNA fragment which is from a microorganism or from a closely related microorganism.

In general, the DNA sequences have only few alterations and can hybridize to one another.

NON-HOMOLOGOUS DNA: Is a DNA fragment which in general does not hybridize with a DNA segment.

VECTOR: This is a DNA segment which can replicate itself in a host by utilizing the host's machinery. Vectors are useful as cloning tools for replicating other DNA segments fused thereto.

FUNCTIONAL EQUIVALENT DNA SEGMENTS: These are DNA sequences which may have a certain percentage of variation from one another while still preserving a defined characteristic, e.g., translation into a polypeptide, hybridization to a specific DNA segment, and the like.

ACTIVE DNA FRAGMENTS: These are portions of a DNA segment of a lesser number of bases which still preserve a certain characteristic possessed by the complete segment, e.g., hybridization to a determined DNA.

NUCLEOTIDE: Is the basic molecule of DNA and is made up of a base, a sugar and a phosphate group.

DEOXYRIBONUCLEIC ACID (DNA): This is a double-stranded chain of deoxyribonucleotides. Each nucleotide in one strand has a corresponding or complementary nucleotide at the same position of the opposite strand. Some DNAs encode proteins, with each trinucleotide encoding a single amino acid.

RIBONUCLEIC ACID (RNA): This is a chain of ribonucleotides.

OLIGONUCLEOTIDE: This is a portion of a DNA fragment consisting of a few to several hundred nucleotides.

NUCLEOTIDE SEQUENCE: This is a linear chain of nucleotides along a DNA strand in the exact order of their appearance in a DNA fragment.

RESTRICTION ENDONUCLEASES: These are enzymes that cut or restrict the DNA molecule into oligonucleotide fragments. Each enzyme cuts at specific and constant sites LIGATION: This is a process whereby an enzyme or a ligase splices or ligates together two or more DNA fragments by means of a chemical bond.

VECTOR: This is a DNA sequence or molecule that can autonomously replicate in a host. Examples are plasmids and viruses.

GENETIC ENGINEERING/RECOMBINANT DNA: Technology relying on the manipulation of a DNA fragment from one source that is transferred to and can replicate in a host. Typically, a DNA fragment of choice is restricted from a larger DNA molecule, ligated to an appropriately restricted vector, and transformed into a new host cell.

CLONE: This term refers to a population of cells whose members carry one or more copies of a specific recombinant DNA fragment.

PLASMID DNA: This is a segment of DNA which is carried by the host not as part of its genome but as separate therefrom.

GENE LIBRARY OR GENE BANK: This is a collection of clones representing all or a considerable portion of the DNA contained in an organism.

GENE: This term describes a DNA sequence that contains information for construction of a polypeptide or protein. It includes 5' and 3' ends thereof.

SUBCLONING: This term refers to a process of removing extraneous DNA from a recombinant DNA fragment.

HYBRIDIZATION: By this is meant the formation of a double stranded DNA between two single strands of DNA or one RNA and one DNA strand derived from the same or different sources PROBE: Is a DNA fragment labeled for purposes of monitoring hybridization reactions.

POLYMERASE CHAIN REACTION (PCR): This term refers to a process of enzymatic amplification of a portion of a DNA fragment. The portion that is amplified is selected by the choice of primers that flank each side of the DNA to be amplified.

PRIMER: Is an oligonucleotide that will allow the polymerase chain reaction to proceed, if its sequence is identical, or nearly so, to that of the two regions that flank the region of the DNA to be amplified.

EXPRESSION VECTOR: Is a cloning vector which contains a strong promoter. Such a vector can allow the efficient transcription of a gene inserted into it, and is useful when the objective of cloning is to obtain high levels of a particular gene product.

PROMOTER: Can be inserted into a DNA strand. A promoter is a nucleotide sequence which is recognized and bound by a DNA-dependent RNA polymerase during the initiation of transcription. It is usually in the 5' region of a gene and is located proximal to the start codon.

TRANSCRIPTION: Is the synthesis of an RNA strand from a complementary DNA strand in a process in which ribonucleotide 5'-triphosphates bases pair sequentially with nucleotides in a template strand (the DNA strand) and are polymerized in the 5' to 3, direction by an RNA polymerase.

TERMINATOR: Is a segment of DNA that specifies the termination of a transcriptional signal. The secondary structure in the transcript itself appears to be important in effecting termination. In bacteria terminators vary in efficiency and in mechanism of action.

TRANSFORMATION: Is a procedure by which exogenous DNA is taken up by a recipient or host cell. The exogenous DNA may be incorporated into the chromosome or a plasmid of the host by homologous recombination, or it may be converted into an autonomous replicon.

REPLICON: Is any DNA fragment or molecule which possesses a replication origin and which is therefore potentially capable of being replicated in a suitable cell.

STRUCTURAL GENE: Is a DNA sequence that may be transcribed into a messenger RNA, which may then be translated into a specific polypeptide having a characteristic sequence of amino acids.

HETEROLOGOUS DNA: Is a DNA fragment which is foreign to, or originates from a different organism than, the host, chemically synthesized gene or fragments thereof. A heterologous gene or fragments thereof code for polypeptides ordinarily not produced by the organism susceptible to transformation by the expression vector or by other structural genes cloned therein.

OPERABLY LINKED: Is the in-frame splicing of a DNA segment such that the promoter controls the initiation of the expression of the polypeptide encoded by the structural gene.

EXPRESSION: Is a process by which a structural gene produces a polypeptide. The process involves transcription of the gene into a messenger RNA (mRNA) and translation thereof into a polypeptide chain.

VEHICLE: Is the organism in which a recombinant DNA molecule is replicated during cloning experiments.

CLONING (OF DNA): Is an in vitro procedure in which a particular DNA sequence, e.g., a gene or fragments thereof, is reproduced in large amounts by inserting or splicing it into a suitable replicon (the vector or cloning vector), introducing the resulting recombinant or hybrid molecule into a host cell where it can replicate, and finally growing the cells in culture. The DNA to be cloned, e.g., the donor, exogenous, or foreign DNA, may be obtained by extracting DNA from an organism and subjecting it to mechanical shearing or endonuclease enzyme action. The vector is typically either a plasmid or a viral genome.

INDUCIBLE: It is said that a gene or gene-product is inducible if its transcription or synthesis is enhanced or increased by exposure of the cells to an effector. An inducible heat-shock promoter is induced by the presence of high temperature which effects significant changes in the regulatory factors governing increased transcription rates.

GRAM NEGATIVE: Cells which lose the primary violet or blue color during decolorization in Gram's staining method. The method, developed by Hans Gram, a Danish physician, in 1884, gives a simple and convenient distinction between groups of bacteria. The staining reaction reflects differences in cell wall composition, but the mechanism is not clear.

GRAM POSITIVE: Cells which retain the primary violet or blue stain in Gram's method.

IN VITRO: In latin it means "in glass", that is to say not in a living animal or person.

IN VIVO: In latin it means in a living animal or person.

PATHOGENIC: This term refers to the production of disease or pathological changes.

IN-FRAME: It is said that two oligonucleotide open reading frames maintain their single contiguous open reading frames after ligation if the ligated product contains the same sequence of amino acids as that of the two separate oligonucleotide-coded products.

FUSION: Is a process of in-frame ligation.

OPERON: Is a fusion of two (bicistronic) or more genes with the same transcriptional unit. Their coordinate transcriptional regulation is implied of all genes contained within the same operon.

PROCARYOTIC: This term encompasses technology related to bacteria (without nuclei)

EUCARYOTIC: This term relates to organisms more advanced than bacteria (with nuclei).

A more complete appreciation of the invention and many of the attendant advantages thereof will be readily perceived as the same becomes better understood by reference to the following detailed description when considered in connection with the accompanying figures.

Other objects advantages and features of the present invention will become apparent to those skilled in the art from the following discussion.

BEST MODE FOR CARRYING OUT THE INVENTION

This invention arose from a desire by the inventors to improve on prior art technology and to develop a probe to identify enteroaggregative E. coli bacteria in biological samples without the drawbacks associated with the known tissue culture procedure.

The present probe is a DNA segment capable of identifying enteroaggregative E. coli bacteria with high sensitivity and a specificity of up to 90%, and sometimes greater sensitivity, when compared with the HEp-2 tissue culture cell assay known in the art. The probe disclosed herein has been shown to have 90% specificity for enteroaggregative E. coli bacteria and to rarely hybridize with DNAs of other bacteria including enterotoxigenic, enteroinvasive, enterohemorrhagic and enteropathogenic E. coli or strains of E. coli exhibiting diffuse adherence.

This invention provides an oligonucleotide which comprises a DNA segment capable of hybridizing to DNA from enteroaggregative E. coli bacteria with high sensitivity and specificity.

In a preferred embodiment the DNA segment comprises about 20 to 6,500 DNA bases, and more preferably about 20 to 400, about 400 to 1,500 and about 1,500 to 6,500 DNA bases, and still more preferably about 20 bases to 1 Kbase. Moreover, the oligonucleotide may contain additional sequences and will typically have up to about 500 bases, and preferably up to about 300 bases. Preferred are the smaller size fragments.

In a most preferred embodiment the DNA fragment has 776 base pairs, functional equivalents thereof or functional fragments thereof about 10 to 500 base pairs long, and more preferably about 20 to 350 base pairs. A still more preferred embodiment is that where the DNA fragment has the sequence.

TABLE 4

| | | | Sequence of EcoRI/PstI DNA Fragment | | | |
|---|---|---|---|---|---|---|
| 1 | CCCGGGGATC | GAGTGAGACA | CATATTATAC | TCATTTCTTG | CAATAAATGC | TTATCTGTTT |
| 61 | TCGACACAGA | CTCTGGCGAA | AGACTGTATC | ATTGATAATT | TCTTTCAGAA | AAGCATCCAG |
| 121 | TTTAATTCTT | ATTCTCTTGA | TATCGAAGAG | TTAGATATTA | ATAAACATAA | CAATATAAAA |
| 181 | ACGATGTTAC | CAGATATAAA | TATAGGGTTA | GGGCAGTATA | TAAACAACAA | TCAATGGTTC |
| 241 | TCATCTATTA | CAGACAGCCA | TTTTTATTTA | TCATTATCCT | ATAATCTTCT | ATCGGCTTAT |
| 301 | GAAGCAAAAA | TGCAGAATAA | TAAATTGGAT | ATTGCTAATT | ATTTAAAATA | TATTGAAATG |
| 361 | CTTAGTGAGA | GGAACAACTA | CATAATTAAT | TTGTTCTCGG | AAATTATTAA | CTATAAGATA |
| 421 | AAAAAATCTC | ACCTGATGTT | GATGCTCGAG | AGATATAGGA | AGCTCAATAA | AGAATACGAA |
| 481 | ATTGCAAAGC | ATAAATGTC | AATTGGATTA | ATATCTGCTC | TTGATGTAGA | GATGATATAT |
| 541 | AATATTTTAC | AAAAAATCAG | GTTTGATATT | GATGTCCTTG | AGGAGGAGGA | AAGTTTACTG |
| 601 | TCAGATAAAA | TCTCGAGAGA | ATATCATGTT | CCTGAGAGTG | CAATCCCAGA | CATTACATAT |
| 661 | CATAAGTTAA | AAGAGTGTAA | AACAGCGGAT | TTCTATACAT | TATTAGCTGA | AAACAAAAAA |
| 721 | CTCAAGATTA | AGGCTGCTGA | TATAGATAAT | GATATAAGGA | AACTATCTGA | GATCCT | functional equivalents thereof or functional fragments thereof as described above.

The fragments of this DNA segment are functional in the sense that they hybridize with the specificity and sensitivity of the DNA segment of the invention. By functional equivalents of the DNA sequences is intended any redundant DNA sequences which preserve the sensitivity and specificity characteristics of the present probe. More particularly, substitutions of up to about 20% of the bases still preserve the hybridization characteristics of the present probe, and more preferably variations of up to about 10% of the DNA sequence.

In another preferred embodiment the DNA probe of this invention hybridizes with high sensitivity and specificity to a DNA segment of enteroaggregative E. coli (EAggEC) associated with the adherence property. Still more preferred, the present probe hybridizes to EAggEC DNA carried by the bacterium as a plasmid.

In still another preferred embodiment the DNA segment comprised in the oligonucleotide of the invention has the enzyme restriction map of the 6.5 Kbase DNA fragment shown in FIG. 2, active fragment thereof and functional equivalents thereof.

The DNA fragments may typically be about 200 to 1,200 bases long, and more preferably about 400 to 1,000 bases long. Still more preferred is a DNA segment about 776 base pairs long of the sequence shown above. The size and number of base pairs of the fragments still permits the identification of specific EAggEC adherence sequences and their hybridization thereto. Another preferred fragment has about 1.0 Kbases. Synthetic DNA fragments can be prepared by known technology of about as low as 20 bases long or less.

The oligonucleotide comprising the DNA segment is provided either as single or double stranded DNA, which may optionally be labeled by methods known in the art. By means of example a $^{32}P$ label may be utilized. Another label may be a protein such as biotin or an enzyme such as alkaline phosphatase. Other labels may also be utilized as is known in the art.

Typically, the DNA segment of the invention may exhibit a sensitivity for enteroaggregative E. coli DNA in a hybridization assay of up to about 80%, or greater, and in some instances up to about 90%, or greater. The oligonucleotide of the invention may have a specificity for enteroaggregative E. coli DNA of up to about 95%, or greater, and in some instances up to about 98%, or greater.

In one particularly preferred embodiment of the invention, the oligonucleotide of the invention comprises a DNA segment which is selected from the group consisting of the DNA segment cloned into the pCVD432 plasmid which is carried in a DH5 host having the ATCC Accession No. 67963, active fragments thereof and functional equivalents thereof. A most preferred oligonucleotide is the oligonucleotide being carried by the deposited host described above. Another most preferred embodiment is that where the oligonucleotide comprises the DNA sequence shown above.

In a most preferred embodiment the oligonucleotide of the invention comprises a DNA segment which is capable of specifically discriminating between enteroaggregative E. coli and enteroaggregative E. coli homologous DNA on one hand, and non-enteroaggregative E. coli homologous DNA. In a still more preferred embodiment the DNA segment comprised in the oligonucleotide hybridizes to enteroaggregative E. coli DNA but does not hybridize to DNA from bacteria selected from the group consisting of enteropathogenic, enterotoxicogenic, enteroinvasive and enterohemorrhagic E. coli bacteria and DNA from E. coli exhibiting diffuse adherence. In a still more preferred embodiment the oligonucleotide of the invention fails to substantially hybridize to non-enteroaggregative E. coli bacteria while hybridizing to enteroaggregative E. coli and enteroaggregative E. coli-homologous DNA.

The sequence of a DNA fragment specific to EAggEC is shown in the examples. However, the present invention encompasses equivalent DNA fragments which have from 0 to 20% sequence discordance or variation and more preferably about 2 to 10% discordance or variation. These fragments may be synthesized by methods known in the art. The fragments encompassed herein are capable of specifically hybridizing to EAggEC DNA by applying technology also known in the art and may be utilized as described in this patent. The sequence of other related DNA fragments may also be determined with technology known in the art.

Also provided herein is a recombinant vector which comprises a vector carrying the oligonucleotide of the invention, the vector being capable of replication in a host. In a particularly preferred embodiment the vector is capable of high levels of replication in the host. By means of example, the vector may be a multiple copy type vector or it may carry multiple copies of the present oligonucleotide. The vector carries all necessary sequences for DNA replication.

Particularly preferred is the vector used in the present examples. However, other vectors may also be utilized. Different suitable types of vectors are known in the art which may be used for replicating DNA segments fused to the vector, and optionally expressing their products, in hosts such as prokaryotic hosts. Also known are methods for cloning DNA segments into vectors, for transformation of a host and other related technologies.

Other vectors for use with eurokaryotic hosts are also known in the art as are methods for cloning DNA fragments into eukaryotic vectors, and for the transformation of eukaryotic hosts.

The vector may be, e.g., a plasmid or a virus, which can insert itself in the corresponding host, grow and replicate itself and any DNA segments fused thereto, and optionally express gene products encoded by the fused DNA segment. Examples of such vectors are pBR322, pUC19 and cosmid vectors such as pHC79. Other vectors, however, may also be utilized depending on the type of host cell available.

In one particularly preferred embodiment of the invention the recombinant vector is pCVD432. This vector carries the about 1 Kb DNA fragment described in the examples. Other recombinant vectors can be obtained by cloning smaller DNA subfragments into a vector. The smaller subfragments can be obtained by enzyme restriction with one or more enzymes. Starting from the recombinant vector, the about 1 Kb fragment can be obtained by double restriction with EcoRI and PstI. In another embodiment the vector is pBB1722 and it carries the about 1 Kb DNA fragment.

In a particularly preferred embodiment the oligonucleotide of the invention comprises a DNA segment which is obtained, e.g., by isolating a sequence of DNA that is specific for E. coli manifesting aggregative adherence. The isolated DNA is then made single stranded and provided with a marker such as $^{32}$P, biotin or alkaline phosphatase by methods known in the art.

In a most preferred embodiment the recombinant vector comprises a vector capable of replicating in a host, and attached thereto a DNA fragment having the sequence

| 1   | CCCGGGGATC | GAGTGAGACA | CATATTATAC | TCATTTCTTG | CAATAAATGC | TTATCTGTTT |
|-----|------------|------------|------------|------------|------------|------------|
| 61  | TCGACACAGA | CTCTGGCGAA | AGACTGTATC | ATTGATAATT | TCTTTCAGAA | AAGCATCCAG |
| 121 | TTTAATTCTT | ATTCTCTTGA | TATCGAAGAG | TTAGATATTA | ATAAACATAA | CAATATAAAA |
| 181 | ACGATGTTAC | CAGATATAAA | TATAGGGTTA | GGGCAGTATA | TAAACAACAA | TCAATGGTTC |
| 241 | TCATCTATTA | CAGACAGCCA | TTTTTATTTA | TCATTATCCT | ATAATCTTCT | ATCGGCTTAT |
| 301 | GAAGCAAAAA | TGCAGAATAA | TAAATTGGAT | ATTGCTAATT | ATTTAAAATA | TATTGAAATG |
| 361 | CTTAGTGAGA | GGAACAACTA | CATAATTAAT | TTGTTCTCGG | AAATTATTAA | CTATAAGATA |
| 421 | AAAAAATCTC | ACCTGATGTT | GATGCTCGAG | AGATATAGGA | AGCTCAATAA | AGAATACGAA |
| 481 | ATTGCAAAGC | ATAAAATGTC | AATTGGATTA | ATATCTGCTC | TTGATGTAGA | GATGATATAT |
| 541 | AATATTTTAC | AAAAAATCAG | GTTTGATATT | GATGTCCTTG | AGGAGGAGGA | AAGTTTACTG |
| 601 | TCAGATAAAA | TCTCGAGAGA | ATATCATGTT | CCTGAGAGTG | CAATCCCAGA | CATTACATAT |
| 661 | CATAAGTTAA | AAGAGTGTAA | AACAGCGGAT | TTCTATACAT | TATTAGCTGA | AAACAAAAAA |
| 721 | CTCAAGATTA | AGGCTGCTGA | TATAGATAAT | GATATAAGGA | AACTATCTGA | GATCCT     | functional equivalents thereof or functional fragments thereof about 10 to 500 bases long, and more preferably 20 to 350 bases long.

Also provided herein is a host carrying the recombinant vector of the invention. Typical hosts are bacteria, yeast cells, eukaryotic cells and the like. In a particularly preferred embodiment, specific bacteria such as, e.g., HB101 or DH5 are utilized. However, other hosts may also be utilized within the confines of this invention. In the present examples the DH5 host was utilized.

A most preferred embodiment is a DH5 host transformed with the vector described above which has been deposited with the ATCC in Rockville, Md. under the Accession No. 67963. This is a DH5 host carrying the recombinant plasmid pCVD432.

The recombinant vector of the invention is manufactured by the implementation of techniques essentially known in the art (e.g., Maniatis, T., Fritsch, E. F., and Sambrook, J., "Molecular Cloning : A Laboratory Manual, Cold Spring Harbor Laboratory", Cold Spring Harbor, New York (1982), the entire text of which is incorporated herein by reference).

The host may be transformed with the recombinant vector by methods known in the art. Any method suitable for particular recombinant vector and host may be utilized herein. Typically, known procedures are available in the art for transformation of bacteria, yeast and eurokaryotic cells (Maniatis et al, 1982, supra; Upcroft, P. et al, "Transduction of a Bacterial Gene into Mammalian Cells, PNAS (USA) 75:2117-2121 (1978); Hinnen, A. et al, "Transformation of Yeast", PNAS USA) 75:1929-1933 (1978), the entire contents of which are incorporated herein by reference).

A particularly preferred embodiment is that of a host which has been transformed with a vector capable of replication in the host that carries the following DNA sequence functional equivalents thereof or functional fragments thereof about 10 to 500 bases long, and more preferably about 50 to 350 bases long.

Test samples suspected of containing aggregative E. coli bacteria are grown under conditions effective for developing bacterial colonies. For example, biological samples may be grown on MacConkey agar for a period of about 18 to 24 hours at about 35° C. However, other conditions known in the art may also be utilized.

The thus obtained bacterial colonies may then be, e.g., attached to a filter paper and then treated with alkali and heated to rupture the bacterial cells, release the bacterial DNA, denature the DNA by separating the two strands and fixing it to the filter paper. Other methods may also be utilized as are known in the art. The filter paper can then be reacted with a labeled oligonucleotide probe in accordance with this invention in single stranded form. If the DNA probe finds homologous sequences in the DNA from one or more of the bacterial colonies on the filter it hybridizes thereto and resists removal upon washing. Similar technology is available for the detection of RNA segments in a biological sample.

The washed filter may then be developed to detect the marker attached to the DNA probe, which thus permits the identification of the bacterial colony obtained from the biological sample as positive or negative. (Kaly, R. G., et al, "Enzymatic Synthesis of Deoxyribonucleic Acid",J.Biol.Chem.245:39-45 (1970); Hames,B. D., and Higgins,S. J.,Eds., "Nucleic Acid Hybridization: A Practical Approach", IRL Press, Oxford (1985), the entire texts of which are incorporated herein by reference).

The DNA probe of the invention may be obtained among others, by the following method. Several fragments, e.g., about 1 kilobase (Kb) long, may be isolated from the aggregative E. coli strain 042 plasmid as previously described (Vial,P.A., et al., supra) after several rounds of enzyme restrictions. The isolated fragments may then be evaluated as potential probes for aggregative E. coli. The specificity of strain 042 fragment being 50% proved to be too low to be useful for specifically

| 1   | CCCGGGGATC | GAGTGAGACA | CATATTATAC | TCATTTCTTG | CAATAAATGC | TTATCTGTTT |
|-----|------------|------------|------------|------------|------------|------------|
| 61  | TCGACACAGA | CTCTGGCGAA | AGACTGTATC | ATTGATAATT | TCTTTCAGAA | AAGCATCCAG |
| 121 | TTTAATTCTT | ATTCTCTTGA | TATCGAAGAG | TTAGATATTA | ATAAACATAA | CAATATAAAA |
| 181 | ACGATGTTAC | CAGATATAAA | TATAGGGTTA | GGGCAGTATA | TAAACAACAA | TCAATGGTTC |
| 241 | TCATCTATTA | CAGACAGCCA | TTTTTATTTA | TCATTATCCT | ATAATCTTCT | ATCGGCTTAT |
| 301 | GAAGCAAAAA | TGCAGAATAA | TAAATTGGAT | ATTGCTAATT | ATTTAAAATA | TATTGAAATG |
| 361 | CTTAGTGAGA | GGAACAACTA | CATAATTAAT | TTGTTCTCGG | AAATTATTAA | CTATAAGATA |
| 421 | AAAAAATCTC | ACCTGATGTT | GATGCTCGAG | AGATATAGGA | AGCTCAATAA | AGAATACGAA |
| 481 | ATTGCAAAGC | ATAAAATGTC | AATTGGATTA | ATATCTGCTC | TTGATGTAGA | GATGATATAT |
| 541 | AATATTTTAC | AAAAAATCAG | GTTTGATATT | GATGTCCTTG | AGGAGGAGGA | AAGTTTACTG |
| 601 | TCAGATAAAA | TCTCGAGAGA | ATATCATGTT | CCTGAGAGTG | CAATCCCAGA | CATTACATAT |
| 661 | CATAAGTTAA | AAGAGTGTAA | AACAGCGGAT | TTCTATACAT | TATTAGCTGA | AAACAAAAAA |
| 721 | CTCAAGATTA | AGGCTGCTGA | TATAGATAAT | GATATAAGGA | AACTATCTGA | GATCCT     | detecting aggregative *E. coli* but served as a tool in the search for a more specific probe.

Plasmid DNA from aggregative *E. coli* strain 17-2 may be isolated and restricted using different restriction enzymes as exemplified in the Figures. However, other enzymes can be utilized which will result in DNA fragments of any desired size, specificity and sensitivity. In the present examples, the smallest fragment hybridizing with the 1 Kb 042 fragment obtained with the enzyme EcoRI is an EcoRI fragment of about 6.5 Kb (see FIG. 1). This about 6.5 Kb fragment, or other fragments obtained in accordance to this invention, may be, e.g., purified by gel electrophoresis, electroelution and cloning into a vector, such as pUC19. The same procedure may be repeated on the subclone using other restriction enzymes, and any smaller fragments hybridizing with the 042 DNA fragment may be detected with a label.

In the present examples, the smallest fragment obtained was one of about 1 Kb, and it was obtained by restriction with the enzyme Sau3A (see FIG. 2) However, other enzymes will yield other suitable fragments as well. The thus obtained fragments may be purified as described above and further subcloned in, e.g., the BamHI site of a vector, such as pUC19. The recombinant plasmid obtained in the examples is named pCVD432. The aggregative probe fragment of about 1 Kb can be obtained from the pCVD432 plasmid by double restriction with restriction enzymes EcoRI and PstI, gel electrophoresis and separation from the vector by electroelution.

Also provided herein is a method of high sensitivity and specificity for detecting the presence of enteroaggregative *E. coli* DNA in a biologic sample which comprises labeling the oligonucleotide of the invention in single stranded form, a functional fragment thereof or a functional equivalent thereof;

adding to the sample the labeled oligonucleotide to promote hybridization thereof to the sample's DNA; and detecting the presence of hybridized labeled DNA.

In a particularly preferred embodiment the above method further comprises treating the sample under conditions effective to expose single stranded cellular DNA prior to adding the labeled oligonucleotide. This can be done by means known in the art, such as by adding sodium hydroxide to the biological sample. (Grunstein, M., Hogness, D. "Colony hybridization: a method for the isolation of cloned DNAs that contain a specific gene", PNAS (USA) 72:3961 (1975), the entire text of which is incorporated herein by reference).

The method of this invention may also comprise treating the sample under conditions effective for cell lysis and release of the nucleic acids into an appropriate medium and/or introducing into an aqueous medium, e.g., two short unlabeled oligonucleotide fragments (primers) which are also part of the invention and/or amplifying any DNA present in the sample by the polymerase chain reaction (Saiki, R. K., et al, "Enzymatic Amplification of Beta-Globin Genomic Sequences and Restriction Site Analysis for Diagnosis of Sickle-Cell Anemia", Science 230:1350–1354 (1985), the entire content of which is incorporated herein by reference). The detection of hybrid radiolabeled DNA may be conducted by methods that are standard in the art, whether or not a nucleic acid fragment defined at both ends by the choice of primers has been amplified.

Also provided herein is a sensitive and specific method of detecting the presence of enteroaggregative *E. coli* RNA in a sample, which comprises labeling the oligonucleotide of the invention in single stranded form;

adding to the sample the labeled oligonucleotide to promote hybridization thereof to the sample's RNA; and detecting the presence of hybridized labeled RNA-DNA hybrid.

The hybridization conditions for both DNA-DNA and DNA-RNA are known in the art and need not be further described herein. More or less stringent conditions may be utilized as desired by a practitioner.

In a preferred embodiment, the above method further comprises treating the sample under conditions effective to expose single stranded cellular RNA prior to adding the labeled oligonucleotide. This may be done by methods known in the art, which thus need not be described herein further.

In still another preferred embodiment the method described above further comprises amplifying the sample's RNA prior to adding the labeled oligonucleotide. Also, in this case, methods are known in the art for conducting the amplification of RNA.

In a particularly preferred embodiment of the above methods the oligonucleotide utilized to promote hybridization with the RNA or DNA of a biological sample comprises the DNA sequence

|     |            |            |            |            |            |            |
|-----|------------|------------|------------|------------|------------|------------|
| 1   | CCCGGGGATC | GAGTGAGACA | CATATTATAC | TCATTTCTTG | CAATAAATGC | TTATCTGTTT |
| 61  | TCGACACAGA | CTCTGGCGAA | AGACTGTATC | ATTGATAATT | TCTTTCAGAA | AAGCATCCAG |
| 121 | TTTAATTCTT | ATTCTCTTGA | TATCGAAGAG | TTAGATATTA | ATAAACATAA | CAATATAAAA |
| 181 | ACGATGTTAC | CAGATATAAA | TATAGGGTTA | GGGCAGTATA | TAAACAACAA | TCAATGGTTC |
| 241 | TCATCTATTA | CAGACAGCCA | TTTTTATTTA | TCATTATCCT | ATAATCTTCT | ATCGGCTTAT |
| 301 | GAAGCAAAAA | TGCAGAATAA | TAAATTGGAT | ATTGCTAATT | ATTTAAAATA | TATTGAAATG |
| 361 | CTTAGTGAGA | GGAACAACTA | CATAATTAAT | TTGTTCTCGG | AAATTATTAA | CTATAAGATA |
| 421 | AAAAAATCTC | ACCTGATGTT | GATGCTCGAG | AGATATAGGA | AGCTCAATAA | AGAATACGAA |
| 481 | ATTGCAAAGC | ATAAAATGTC | AATTGGATTA | ATATCTGCTC | TTGATGTAGA | GATGATATAT |
| 541 | AATATTTTAC | AAAAAATCAG | GTTTGATATT | GATGTCCTTG | AGGAGGAGGA | AAGTTTACTG |
| 601 | TCAGATAAAA | TCTCGAGAGA | ATATCATGTT | CCTGAGAGTG | CAATCCCAGA | CATTACATAT |
| 661 | CATAAGTTAA | AAGAGTGTAA | AACAGCGGAT | TTCTATACAT | TATTAGCTGA | AAACAAAAAA |
| 721 | CTCAAGATTA | AGGCTGCTGA | TATAGATAAT | GATATAAGGA | AACTATCTGA | GATCCT      | functional fragments thereof or functional equivalents thereof as described above.

Also provided by this invention is a kit, comprising in separate containers the oligonucleotide of the invention; and an auxiliary component selected from the group consisting of filter paper, denaturing solution, rinsing solution, a radiolabel, and the like, known in the art for use in DNA or RNA hybridization.

The kit may also comprise a further oligonucleotide comprising a further DNA segment selected from the group consisting of enteropathogenic, enterotoxicogenic, enteroinvasive and enterohemorrhagic E. coli DNA and E. coli DNA exhibiting diffuse adherence.

This kit may be utilized for screening large numbers of biological samples by first testing all samples by practicing the method described above for hybridizing enteroaggregative E. coli DNA with the aid of the necessary laboratory elements such as filter paper or other hybridization supports, denaturing solution, rinsing solution, and the like.

In one particularly preferred embodiment of the invention the kit provided herein comprises the oligonucleotide of the invention in labeled form. Suitable labels are known in the art and examples were given above.

In another preferred embodiment of the invention the EAggEC oligonucleotide probe in the kit is labeled, and optionally frozen, freeze dried or iced.

In a particularly preferred embodiment of the invention the oligonucleotide comprises the DNA sequence

| 1 | CCCGGGGATC | GAGTGAGACA | CATATTATAC | TCATTTCTTG | CAATAAATGC | TTATCTGTTT |
|---|---|---|---|---|---|---|
| 61 | TCGACACAGA | CTCTGGCGAA | AGACTGTATC | ATTGATAATT | TCTTTCAGAA | AAGCATCCAG |
| 121 | TTTAATTCTT | ATTCTCTTGA | TATCGAAGAG | TTAGATATTA | ATAAACATAA | CAATATAAAA |
| 181 | ACGATGTTAC | CAGATATAAA | TATAGGGTTA | GGGCAGTATA | TAAACAACAA | TCAATGGTTC |
| 241 | TCATCTATTA | CAGACAGCCA | TTTTTATTTA | TCATTATCCT | ATAATCTTCT | ATCGGCTTAT |
| 301 | GAAGCAAAAA | TGCAGAATAA | TAAATTGGAT | ATTGCTAATT | ATTTAAAATA | TATTGAAATG |
| 361 | CTTAGTGAGA | GGAACAACTA | CATAATTAAT | TTGTTCTCGG | AAATTATTAA | CTATAAGATA |
| 421 | AAAAAATCTC | ACCTGATGTT | GATGCTCGAG | AGATATAGGA | AGCTCAATAA | AGAATACGAA |
| 481 | ATTGCAAAGC | ATAAATGTC | AATTGGATTA | ATATCTGCTC | TTGATGTAGA | GATGATATAT |
| 541 | AATATTTTAC | AAAAAATCAG | GTTTGATATT | GATGTCCTTG | AGGAGGAGGA | AAGTTTACTG |
| 601 | TCAGATAAAA | TCTCGAGAGA | ATATCATGTT | CCTGAGAGTG | CAATCCCAGA | CATTACATAT |
| 661 | CATAAGTTAA | AAGAGTGTAA | AACAGCGGAT | TTCTATACAT | TATTAGCTGA | AAACAAAAAA |
| 721 | CTCAAGATTA | AGGCTGCTGA | TATAGATAAT | GATATAAGGA | AACTATCTGA | GATCCT | functional fragments thereof or functional equivalents thereof as defined above.

Having now generally described this invention, the same will be better understood by reference to certain specific examples, which are included herein for purposes of illustration only and are not intended to be limiting of the invention or any embodiment thereof, unless so specified.

EXAMPLES

Example 1: Bacterial Strains

The EAggEC strains used in this study were originally collected from children under 24 months of age with diarrhea during the course of epidemiological surveys in Chile (Levine, M. M., Prado, V., Robins-Browne, R. M., Lior, H., Kaper, J. B., Moseley, S., Gicquelais, K., Nataro, J. P., Vial, P., Tall, B., "Use of DNA probes and HEp-2 cell adherence assay to detect diarrheagenic E. coli", J. Infect. Dis., 158:224–228 (1988)), and in rural India (Bahn, M. K., Raj, P., Levine, M. M., Kaper, J. B., Bhandari, N., Srivastava, R., Kumar, R., Sazawal, S., "Enteroaggregative Escherichia coli associated with persistent diarrhea in a cohort of rural children in India", J. Infect. Dis. (in press 1989)). The Hep-2 cell assay described below was performed to confirm the aggregative pattern.

The non EAgg E. coli were obtained from the reference collection of the Center for Vaccine Development, Baltimore, and included strains from all other class of diarrheagenic E. coli.

A set of 35 E. coli strains collected from age-matched controls during the epidemiological study in Chile was used as representative of normal intestinal flora.

Example 2: Hep-2 cell assay

An adherence assay was performed with monolayers of HEp-2 cells grown on glass coverslips in 24-well tissue culture plates (Costar, Cambridge, MA), as previously described (Vial, P.A., Robins-Browne, R., Lior, H., Prado, V., Kaper, J. B., Nataro, J. P., Maneval, D., Elsayed, A. and Kerine, M. M., "Characterization of EAggEC, a putative agent of diarrheal disease", J. Inf. Diseases 158(1): 70 (1988)).

Briefly, monolayers were inoculated with 20 ul of overnight cultures grown in L broth, and incubated for three hours in the presence of 0.5% methyl-alpha-D-mannoside to prevent attachment by type 1 somatic fimbriae, and then fixed and stained.

Example 3: Isolation of DNA probe

Cesium chloride purified plasmids from EAgg E. coli strain 17-2 was digested with an array of different restriction enzymes, run on a 0.7% agarose gel, and transferred into nitrocellulose filters by the technique of Southern (Southern, E., J. of Molec. Biol. 98:503 (1975)).

Filters were hybridized under stringent conditions with the $^{32}P$ labelled fragment previously isolated from strain 042 (Vial, P.A., et al., supra).

TABLE 1

Agarose Gel of Restricted Plasmid of 17-2 E. coli Strain.

| Lane | Content |
|---|---|
| 1 | molecular weight markers (lambda/HindIII); |
| 2 | 042/HindIII; |
| 3 | p0428/HindIII; |
| 4 | p0428/HindIII; |
| 5 | 17-2/EcoRI; |
| 6 | 17-2/HindIII; |
| 7 | 17-2/SalI; |
| 8 | 17-2/BamHI; |
| 9 | 17-2/XhoI; |
| 10 | 17-2/XbaI; |
| 11 | 17-2/KpnI; |
| 12 | 17-2/SmaI; |
| 13 | molecular weight markers (lambda/HindIII); |
| 14 | 17-2 uncut. |

*about 6.5 kilobase fragment which has been cloned and from which the probe fragment has been obtained.

The cloned 6.5 Kbase EcoRI fragment of the E. coi strain 17-2 plasmid obtained above was subjected to electophoresis on a 0.7% agarose gel. The contents of the lanes are as described in Table 2 below.

TABLE 2

Agarose Gel of Restrictions of the cloned 6.5 Kbase EcoRI Fragment

| Lane | Content |
|---|---|
| 1 | molecular weight markers (lambda/HindIII); |
| 2 | molecular weight markers pBR322/HinfI; |

TABLE 2-continued

Agarose Gel of Restrictions of the cloned 6.5 Kbase EcoRI Fragment

| Lane | Content |
|---|---|
| 3 | cloned EcoRI uncut fragment; |
| 4 | cloned EcoRI fragment/ClaI; |
| 5 | cloned EcoRI fragment/HaeIII; |
| 6 | cloned EcoRI fragment/HindII;I |
| 7 | cloned EcoRI fragment/HpaI; |
| 8 | cloned EcoRI fragment/PstI; |
| 9 | cloned EcoRI fragment/PvuII; |
| 10 | cloned EcoRI fragment/Sau3A; |
| 11 | molecular weight markers (lambda/HindIII); |
| 12 | molecular weight markers pBR322/HinfI. |

*about 1 kilobase Sau3A fragment electroeluted and cloned at the BamHI site of vector pUC19 to give plasmid pBB1722. The insert, cut out with a double digestion by EcoRI and PstI, constitutes the EAggEC probe.

Example 4: Evaluation of Strain 17-2 EAggEC probe

Colonies were transferred to Whatman 541 filters, treated as already described (Mass, R., "An improved colony hybridization method with significantly increased sensitivity for detection of single genes" Plasmid, 10:296-298 (1983)), and were hybridized under stringent conditions with the $^{32}P$ labelled probe.

Example 5: Selection of probe

A 1Kb DNA segment had been obtained by restriction enzyme digestion from the 60 MDa plasmid of EAggEC strain 042 (Vial, P.A., Robins-Browne, R, Lior, H, Prado, V., Kaper, J.B., Nataro, J.P., Maneval, D., Elsayed, A., and Kerine, M.M., "Characterization of EAggEC, a putative agent of diarrheal disease", J. Inf. Diseases 158(1): 70 (1988)).

That isolated EAggEC 042 strain fragment was used to identify an equivalent fragment on the plasmid of EAggEC strain 17-2. This strain was chosen because of its properties as an EAggEC prototype strain.

Among the bands hybridizing strongly with the $^{32}P$ labeled 042 DNA segment, the smallest fragment, a ca. 6.5 Kb EcoRI fragment, was electroeluted and subcloned in the EcoRI site of the vector pUC19 (Yanisch-Perron, C. Vieira, J. and Messing, J., gene 33: 103-119 (1985).

The same procedure was repeated on the subclone. An about 1 Kb Sau3A fragment was found to hybridize strongly with the $^{32}P$ labeled DNA segment from EAggEC strain 042. This 1Kb Sau3A fragment was electroeluted, and subcloned in the BamHI site of the pUC19 plasmid. The resulting plasmid is referred to as pCVD432. The probe fragment can be obtained by double restriction of pCVD432 with restriction enzymes EcoRI and Pst I, and separation from the vector by electroelution from a gel.

Example 6: Sensitivity and specificity of the 1Kb EAggEC fragment

A series of 63 EAggEC strains, 35 normal flora samples, 50 EIEC E. coli strains, 57 EPEC E. coli strains, 43 DA E. coli strains, 143 EHEC E. coli strains and 84 ETEC E. coli strains were tested by the hybridization with the $^{32}P$ labeled fragment of the 17-2 EAggEC strain obtained above.

The results obtained are summarized in Table 1. The 17-2 EAggEC fragment correctly detected 56 of the 63 aggregative strains. This figure is equivalent to an 88% sensitivity.

Moreover, as seen in Table 1, this probe also exhibited a very high specificity: only one control strain from the normal flora out of 35, and 2 out of 50 EIEC strains were detected. None of the 57 EPEC, 43 DA E. coli, 143 EHEC and 84 ETEC reacted positively with the EAggEC probe. This is equivalent to a specificity of 99%.

TABLE 3

Sensitivity and specificity of the EAggEC probe.

| E. coli | No. Strains tested | No. positives obtained (%) |
|---|---|---|
| ETEC | 84 | 0 |
| EIEC | 50 | 2 (4%) |
| EHEC | 143 | 0 |
| EPEC | 57 | 0 |
| DA E. Coli | 43 | 0 |
| Control E. coli | 35 | 1 (2.9%) |
| total | 412 | 3 (<1%) |
| Specificity for EAggEC | | (99%) |
| Sensitivity for EAggEC | 63 | 56 (89%) |

Example 7 Sequence of DNA Fragment

The following DNA sequences were obtained by partial digestion of the about 1Kb DNA fragment. The sequence was determined by restriction of the about 1Kb fragment with the EcoRI and PstI enzymes as described in Example 5 above.

In order to determine its nucleotide sequence the EcoRI-PstI fragment was sucloned into M13mp18 and M13mp19 (Messing, J., "New M13 vectors for cloning", Methods in Enzymology 101:20-78 (1983)).

The nucleotide sequence was determined using the sequenase ® kit (United States Biochemical Corporation, Cleveland, Ohio) and $^{35}S$-dATP following the manufacturer's recommendations. The sequence was determined on both strands for confirmation purposes and is shown in Table 4 below.

TABLE 4

Sequence of EcoRI/PstI DNA Fragment

| 1 | CCCGGGGATC | GAGTGAGACA | CATATTATAC | TCATTTCTTG | CAATAAATGC | TTATCTGTTT |
|---|---|---|---|---|---|---|
| 61 | TCGACACAGA | CTCTGGCGAA | AGACTGTATC | ATTGATAATT | TCTTTCAGAA | AAGCATCCAG |
| 121 | TTTAATTCTT | ATTCTCTTGA | TATCGAAGAG | TTAGATATTA | ATAAACATAA | CAATATAAAA |
| 181 | ACGATGTTAC | CAGATATAAA | TATAGGGTTA | GGGCAGTATA | TAAACAACAA | TCAATGGTTC |
| 241 | TCATCTATTA | CAGACAGCCA | TTTTTATTTA | TCATTATCCT | ATAATCTTCT | ATCGGCTTAT |
| 301 | GAAGCAAAAA | TGCAGAATAA | TAAATTGGAT | ATTGCTAATT | ATTTAAAATA | TATTGAAATG |
| 361 | CTTAGTGAGA | GGAACAACTA | CATAATTAAT | TTGTTCTCGG | AAATTATTAA | CTATAAGATA |
| 421 | AAAAAATCTC | ACCTGATGTT | GATGCTCGAG | AGATATAGGA | AGCTCAATAA | AGAATACGAA |
| 481 | ATTGCAAAGC | ATAAATGTC | AATTGGATTA | ATATCTGCTC | TTGATGTAGA | GATGATATAT |
| 541 | AATATTTTAC | AAAAAATCAG | GTTTGATATT | GATGTCCTTG | AGGAGGAGGA | AAGTTTACTG |
| 601 | TCAGATAAAA | TCTCGAGAGA | ATATCATGTT | CCTGAGAGTG | CAATCCCAGA | CATTACATAT |
| 661 | CATAAGTTAA | AAGAGTGTAA | AACAGCGGAT | TTCTATACAT | TATTAGCTGA | AAACAAAAAA |

TABLE 4-continued

Sequence of EcoRI/PstI DNA Fragment

| 721 | CTCAAGATTA | AGGCTGCTGA | TATAGATAAT | GATATAAGGA | AACTATCTGA | GATCCT |

The invention now being fully described, it will be apparent to one of ordinary skill in the art that many changes and modifications can be made thereto without departing from the spirit or scope of the invention as set forth herein.

We claim:

1. A DNA segment consisting of a DNA sequence with the enteroaggregative *E. coli* DNA hydridizing specificity of the DNA sequence contained in the bacterium ATCC Accession No. CVP-ATCC 67963.

2. An oligonucleotide, consisting of at least one DNA segment of claim 1 with up to about 6,800 DNA bases.

3. The DNA segment of claim 1, being a labeled oligonucleotide.

4. The DNA segment of claim 3, wherein the label comprises $^{32}P$.

5. The DNA segment of claim 1, in single stranded form.

6. The DNA segment of claim 1, having an about 80% or greater sensitivity for enteroaggregative *E. coli* DNA; and an about 95% or greater specificity for enteroaggregative *E. coli*.

7. The DNA segment of claim 1, consisting of the DNA segment carried by the pCVD 432 plasmid.

8. The DNA segment of claim 1, being capable of hybridizing under stringent conditions to enteroaggregative *E. coli* DNA but substantially incapable of hybridizing to DNA from a bacterium selected from the group consisting of enteropathogenic, enterotoxicogenic, enteroinvasive, and enterhemorrhagic *E. coli* bacteria, and *E. coli* bacteria exhibiting diffuse adherence.

9. The DNA segment of claim 8, being capable of hybridizing under stringent conditions to enteroaggregative *E. coli* DNA but substantially incapable of hybridizing to non-enteroaggregative *E. coli* bacteria.

10. The DNA segment of claim 1, having the following DNA sequence

| 1 | CCCGGGGATC | GAGTGAGACA | CATATTATAC | TCATTTCTTG | CAATAAATGC | TTATCTGTTT |
| 61 | TCGACACAGA | CTCTGGCGAA | AGACTGTATC | ATTGATAATT | TCTTTCAGAA | AAGCATCCAG |
| 121 | TTTAATTCTT | ATTCTCTTGA | TATCGAAGAG | TTAGATATTA | ATAAACATAA | CAATATAAAA |
| 181 | ACGATGTTAC | CAGATATAAA | TATAGGGTTA | GGGCAGTATA | TAAACAACAA | TCAATGGTTC |
| 241 | TCATCTATTA | CAGACAGCCA | TTTTTATTTA | TCATTATCCT | ATAATCTTCT | ATCGGCTTAT |
| 301 | GAAGCAAAAA | TGCAGAATAA | TAAATTGGAT | ATTGCTAATT | ATTTAAAATA | TATTGAAATG |
| 361 | CTTAGTGAGA | GGAACAACTA | CATAATTAAT | TTGTTCTCGG | AAATTATTAA | CTATAAGATA |
| 421 | ATTGCAAAGC | ATAAAATGTC | AATTGGATTA | ATATCTGCTC | TTGATGTAGA | GATGATATAT |
| 541 | AATATTTTAC | AAAAAATCAG | GTTTGATATT | GATGTCCTTG | AGGAGGAGGA | AAGTTTACTG |
| 601 | TCAGATAAAA | TCTCGAGGA | ATATCATGTT | CCTGAGAGTG | CAATCCCAGA | CATTACATAT |
| 661 | CATAAGTTAA | AAGAGTGTAA | AACAGCGGAT | TTCTATACAT | TATTAGCTGA | AAACAAAAAA |
| 721 | CTCAAGATTA | AGGCTGCTGA | TATAGATAAT | GATATAAGGA | AACTATCTGA | GATCCT. |

11. A composition, comprising
the oligonucleotide of claim 2; and an acceptable carrier.

* * * * *

UNITED STATES PATENT AND TRADEMARK OFFICE
CERTIFICATE OF CORRECTION

PATENT NO. : 5,189,151
DATED : February 23, 1993
INVENTOR(S) : BAUDRY ET AL.

It is certified that error appears in the above-indentified patent and that said Letters Patent is hereby corrected as shown below:

On the title page, insert the following information:
Assignee: UNIVERSITY OF MARYLAND AT COLLEGE PARK, Maryland 20742, Maryland--

Attorney, Agent, or Firm - FISHER & ASSOCIATES

Signed and Sealed this

Fifteenth Day of August, 1995

Attest:

BRUCE LEHMAN

*Attesting Officer*  *Commissioner of Patents and Trademarks*